United States Patent [19]

Rentzea et al.

[11] Patent Number: 4,497,819

[45] Date of Patent: Feb. 5, 1985

[54] DIBENZOFURANYLOXYALK-YLIMIDAZOLIUM SALTS, THEIR PREPARATION AND THEIR USE AS MICROBICIDES

[75] Inventors: Costin Rentzea, Heidelberg; Norbert Meyer, Ladenburg; Hubert Sauter, Mannheim; Eberhard Ammermann, Ludwigshafen; Ernst-Heinrich Pommer, Limburgerhof, all of Fed. Rep. of Germany

[73] Assignee: BASF Aktiengesellschaft, Fed. Rep. of Germany

[21] Appl. No.: 491,651

[22] Filed: May 5, 1983

[30] Foreign Application Priority Data

May 13, 1982 [DE] Fed. Rep. of Germany ....... 3217963

[51] Int. Cl.³ .................. A61K 31/415; C07D 405/12
[52] U.S. Cl. ...................................... 514/397; 548/336
[58] Field of Search ..................... 548/336; 424/273 R

[56] References Cited

U.S. PATENT DOCUMENTS 4,199,346  4/1980  Saukaitis ................................ 71/88
4,272,545  6/1981  Walker ................................ 548/336

OTHER PUBLICATIONS

Chemical Week, Jun. 21st, 1972, p. 46.

*Primary Examiner*—Alan L. Rotman
*Assistant Examiner*—Dale A. Bjorkman
*Attorney, Agent, or Firm*—Keil & Weinkauf

[57] ABSTRACT

Dibenzofuranyloxyalkylimidazolium salts having the basic skeleton

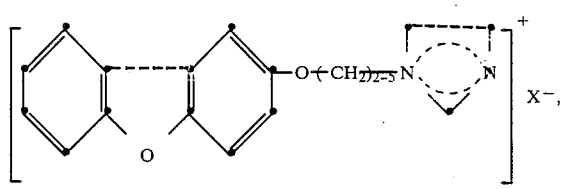

processes for their preparation and their use as microbicides in crop protection, in industry and in human and veterinary medicine.

4 Claims, No Drawings

DIBENZOFURANYLOXYALKYLIMIDAZOLIUM SALTS, THEIR PREPARATION AND THEIR USE AS MICROBICIDES

The present invention relates to novel dibenzofuranyloxyalkylimidazolium salts, processes for their preparation and microbicides, ie. fungicides and bactericides, which contain these compounds as active ingredients.

It has been disclosed that N-trichloromethylthiotetrahydrophthalimide can be used as a fungicide (Chemical Week, June 21st, 1972, page 46), but its activity is not satisfactory in all cases.

It is an object of the present invention to provide a novel class of fungicides which possesses high activity coupled with a broad bactericidal spectrum.

We have found that this object is achieved, and that dibenzofuranyloxyalkylimidazolium salts of the formula

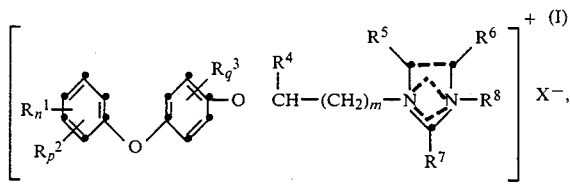

where $R^1$, $R^2$ and $R^3$ are identical or different and are each halogen, unsubstituted or halogen-substituted alkyl or alkoxy, each of 1 to 4 carbon atoms, cyano or nitro, $R^4$, $R^5$, $R^6$ and $R^7$ independently of one another are each hydrogen or alkyl of 1 to 4 carbon atoms, $R^8$ is alkyl, alkenyl or alkynyl, each of not more than 6 carbon atoms,

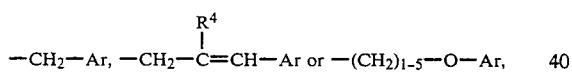

Ar is naphth-1-yl, naphth-2-yl, biphenylyl or phenyl, and the phenyl radical can be substituted by fluorine, chlorine, bromine, nitro, trifluoromethyl, cyano or alkyl, alkenyl or alkoxy of not more than 5 carbon atoms, m is 1, 2, 3 or 4, n, p and q are each 0, 1, 2, or 3, and X is an anion of a monobasic, non-phytotoxic acid or one equivalent of an anion of a polybasic, non-phytotoxic acid, exhibit good fungicidal and bactericidal activity.

Suitable substituents $R^1$, $R^2$ and $R^3$ in formula I are halogen, ie. fluorine, bromine or iodine, nitro, cyano and unsubstituted or halogen-substituted alkyl or alkoxy, each of 1 to 4 carbon atoms, eg. methyl, ethyl, isopropyl, tert.-butyl, methoxy, ethoxy, trifluoromethyl, difluoromethoxy or tetrafluoromethoxy; $R^4$, $R^5$, $R^6$ and $R^7$ are each hydrogen or $C_1$-$C_4$-alkyl, eg. methyl or ethyl; $R^8$ is $C_1$-$C_6$-alkyl, $C_1$-$C_6$-alkenyl or $C_1$-$C_6$-alkynyl, eg. methyl, ethyl, n-propyl, n-butyl, isobutyl, n-pentyl, isopentyl, n-hexyl, vinyl, allyl, but-2-en-1-yl, 3-methylbut-2-en-1-yl or propargyl, or is

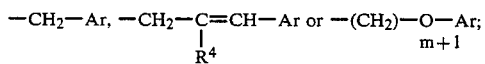

Ar is, for example, naphth-1-yl, naphth-2-yl, biphenylyl, phenyl, 4-fluorophenyl, 3-chlorophenyl, 4-chlorophenyl, 4-bromophenyl, 3,4-dichlorophenyl, 2,4-dichlorophenyl, 2,6-dichlorophenyl, 2-methyl-4-chlorophenyl, 4-methoxyphenyl, 4-ethoxyphenyl, 4-methylphenyl, 4-isopropylphenyl, 4-tert.-butylphenyl, 4-nitrophenyl, 4-trifluoromethylphenyl, 2,4-dimethylphenyl or 4-cyanophenyl; m is 1, 2, 3 or 4; n, p and q are each 0, 1, 2 or 3; and X is an anion of a monobasic, non-phytotoxic acid, or one equivalent of an anion of a polybasic, non-phytotoxic acid, eg. an anion of hydrochloric acid, hydrobromic acid, hydriodic acid, methylsulfuric acid, phenylsulfonic acid, p-methylphenylsulfonic acid, p-dodecylphenylsulfonic acid or nitric acid, or one equivalent of sulfate.

The dibenzofuranyloxyalkylimidazolium salts of the formula I are obtained by a process wherein (a) a compound of the formula

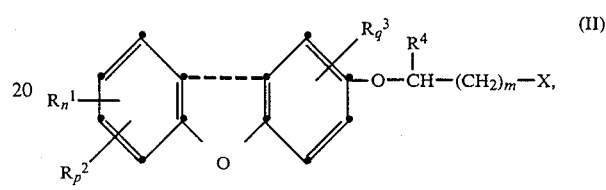

where $R^1$, $R^2$, $R^3$, $R^4$, X, m, n, p and q have the above meanings, is reacted with an imidazole derivative of the formula

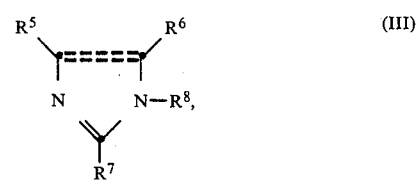

where $R^5$, $R^6$, $R^7$ and $R^8$ have the above meanings, or (b) a compound of the formula

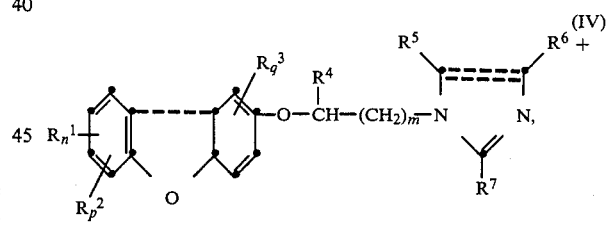

where $R^1$, $R^2$, $R^3$, $R^4$, $R^5$, $R^6$, $R^7$, m, n, p and q have the above meanings, is reacted with a compound of the formula $R^8$—X, where $R^8$ and X have the above meanings.

Reactions (a) and (b) are carried out in the presence or absence of an inert solvent or diluent, at from 20° to 150° C., preferably from 30° to 140° C. The starting material of the formula II is advantageously employed in not more than a 10-fold molar excess, based on the imidazole derivative of the formula III.

Examples of preferred solvents or diluents which are inert to the reactants are aliphatic and aromatic hydrocarbons and aliphatic and aromatic halohydrocarbons, eg. pentane, cyclohexane, benzene, toluene, xylene, chlorobenzene and dichlorobenzenes, aliphatic ketones, eg. acetone, methyl ethyl ketone, diethyl ketone and cyclopentanone, ethers, eg. diethyl ether, dimethoxyethane, tetrahydrofuran and dioxane, esters, eg. ethyl acetate, nitriles, eg. acetonitrile, amides, eg. dimethylformamide, dimethylacetamide and N-methylpyrrolidone, as well as mixtures of these solvents.

The starting materials of the formula II can be readily prepared by a conventional process, for example by etherification of a dibenzofuran-3-ol with an aliphatic dihalide, eg. 1,2-dibromomethane, 1,3-dichloropropane, 1-chloro-3-bromopropane, 1,3-dibromopropane, 1-chloro-4-bromobutane or 1,4-dibromobutane, preferably in boiling methyl ethyl ketone, diethyl ketone or cyclopentanone, in the presence of not less than an equivalent amount of sodium carbonate or potassium carbonate (Houben-Weyl, Methoden der Organischen Chemie, volume 6/3, pages 54–59, Georg Thieme-Verlag, Stuttgart, 1965). Alternatively, a dibenzofuran-3-yloxyalkanol can be reacted with thionyl chloride or with phosphorus tribromide to give a compound of the formula II (Rec. trav. Chim., 76 (1957), 129–146).

The imidazole derivatives of the formula IV can be prepared by a conventional process, for example by alkylating a commercially available imidazole of the formula V, where $R^5$, $R^6$ and $R^7$ have the above meanings, with a compound of the formula II, in accordance with the equation

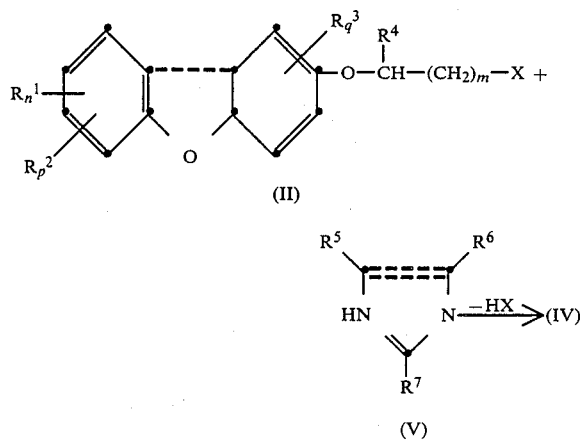

The reaction conditions in this case correspond to those of reaction (a).

The novel imidazolium salts of formula I in which $R^4$ is not hydrogen possess a chiral carbon atom bonded to the ligand $R^4$, and may or may not possess further chiral centers in $R^8$. The optically pure enantiomers or the diastereomers can be obtained by a conventional method. The present invention also embraces these compounds in the pure form or as mixtures. The pure enantiomers or the pure diastereomers as well as the mixtures usually obtained in the synthesis exhibit fungicidal and bactericidal activity.

For example, the following dibenzofuran-3-ols can be employed for the preparation of starting compounds of the formula II or III; dibenzofuran-3-ol, 7-fluorodibenzofuran-3-ol, 7-chlorodibenzofuran-3-ol, 2,4,7-trichlorodibenzofuran-3-ol, 5-chlorodibenzofuran-3-ol, 6-chlorodibenzofuran-3-ol, 8-chlorodibenzofuran-3-ol, 5,7-dichlorodibenzofuran-3-ol, 6,7-dichlorodibenzofuran-3-ol, 7,8-dichlorodibenzofuran-3-ol, 7-bromodibenzofuran-3-ol, 7-methyldibenzofuran-3-ol, 6,8-dichloro-7-methyldibenzofuran-3-ol, 6-trifluoromethyldibenzofuran-3-ol, 7-trifluoromethyldibenzofuran-3-ol, 7-tert.-butyldibenzofuran-3-ol, 7-methoxydibenzofuran-3-ol, 7-chloro-2-nitrodibenzofuran-3-ol and 7-ethoxydibenzofuran-3-ol.

Examples 1 to 52 illustrate the preparation of the compounds of the formula I.

EXAMPLE 1

83 g (0.6 mole) of potassium carbonate were added to a solution of 262 g (1.2 moles) of 7-chlorodibenzofuran-3-ol in 600 ml of dry dimethylformamide, and a solution of 212 g (2.55 moles) of ethylene carbonate in 300 ml of dimethylformamide was then added dropwise in the course of 90 minutes at 100° C. The mixture was stirred for 8 hours at 120° C. and was then filtered under suction at 100° C., and the filtrate was evaporated down. The residue was dissolved in 2.5 liters of ethyl acetate, the solution was washed with three times 300 ml of water, the organic layer was dried, decolorized with 10 g of animal charcoal and evaporated down to 500 ml, and the residue was cooled to 10° C. The precipitate was filtered off under suction, washed with 60 ml of methanol, 50 ml of ether and 200 ml of petroleum ether in succession at +5° C., and dried. 225 g (71.4% of theory) of 2-(7-chlorodibenzofuran-3-yloxy)-ethanol of melting point 118°–120° C. were obtained.

11.9 g (0.15 mole) of pyridine were added to a suspension of 26.2 g (0.1 mole) of 2-(7-chlorodibenzofuran-3-yloxy)-ethanol in 100 ml of dry toluene, and 17.9 g (0.15 mole) of thionyl chloride were then added dropwise at from 3° to 15° C. The mixture was stirred for 1 day at 40° C. and for a further 8 hours at 70° C., after which it was cooled and 150 ml of toluene and 200 ml of ice water were added. The organic layer was washed with 100 ml of water, 50 ml of hydrochloric acid, 50 ml of 1N sodium hydroxide solution and 100 ml of water in succession, and was dried and evaporated down. The solid residue was stirred for 30 minutes with 40 ml of petroleum ether at +3° C. (ice bath), and was then filtered off under suction, washed with a little cold petroleum ether and dried. 22.8 g (81% of theory) of 1-chloro-2-(7-chlorodibenzofuran-3-yloxy)-ethane were obtained at colorless crystals of melting point 105°–107° C.

0.5 g of potassium iodide was added to 19.6 g (0.06 mole) of 1-chloro-2-(7-chlorodibenzofuran-3-yloxy)-ethane and 16.4 g (0.24 mole) of imidazole in 50 ml of dimethylformamide, and the mixture was stirred for 16 hours at 110° C., cooled and then evaporated down under reduced pressure. The residue was partitioned between 100 ml of water and 1 liter of methylene chloride, and 20 ml of 50% strength sodium hydroxide solution were added, while cooling with ice. The organic layer was separated off, washed with three times 50 ml of water, dried, and evaporated down under reduced pressure. The solid, colorless residue was left to stand with 15 ml of ether at +5° C. for 1 hour, after which it was filtered off under suction and washed with 20 ml of cold n-pentane. 13.2 g (70.4% of theory) of N-[2-(7-chlorodibenzofuran-3-yloxy)-ethyl]-imidazole of melting point 150°–151° C. were obtained.

A solution of 15.6 g (0.05 mole) of N-[2-(7-chlorodibenzofuran-3-yloxy)-ethyl]-imidazole and 17.1 g (0.1 mole) of benzyl bromide in 40 ml of dry dioxane and 30 ml of dry acetonitrile was stirred for two days at 70° C. and then cooled to 0° C. The crystalline precipitate was filtered off under suction, washed with 50 ml of dry ether and dried under reduced pressure. 19.7 g (81.5% of theory) of $N^1$-benzyl-$N^3$-[2-(7-chlorodibenzofuran-3-loxy)-ethyl]-imidazolium bromide were obtained as white crystals of melting point 191°–193° C.

EXAMPLE 2

A mixture of 98.4 g (0.45 mole) of 7-chlorodibenzofuran-3-ol, 200 ml of methyl ethyl ketone, 93 g (0.67 mole) of potassium carbonate and 283 g (1.4 moles) of dibromopropane was refluxed for 24 hours, while stirring. The inorganic precipitate was filtered off under suction, the filtrate was evaporated down under reduced pressure, the residue was dissolved in 500 ml of methylene chloride, and the solution was washed with 100 ml of water, 100 ml of 2N sodium hydroxide solution and 100 ml of water in succession, dried over sodium sulfate and evaporated down under reduced pressure. The solid residue was left to stand with 30 ml of pentane at 0° C. for 30 minutes, after which it was filtered off under suction and washed with 30 ml of cold n-pentane. 77 g (50% of theory) of pure 1-bromo-3-(7-chlorodibenzofuran-3-yloxy)-propane of melting point 83°–85° C. were obtained.

A solution of 14 g (0.041 mole) of 1-bromo-3-(7-chlorodibenzofuran-3-yloxy)-propane and 7.9 g (0.05 mole) of N-benzylimidazole in 25 ml of dry dioxane and 25 ml of dry acetonitrile was stirred for 40 hours at 70° C. The mixture was cooled to 15° C. in an ice bath, and the crystalline precipitate formed was then filtered off under suction, washed with 30 ml of ether and finally with 50 ml of n-pentane, and dried. 15 g (73.2% of theory) of $N^1$-benzyl-$N^3$-[3-(7-chlorodibenzofuran-3-yloxy)-propyl]-imidazolium bromide of melting point 162°–166° C. were obtained.

For example, the following compounds of the formula I can be prepared by a procedure similar to that described in Example 1 or 2:

| No. | $R^1$ | $R^4$ | m | $R^5$ | $R^6$ | $R^7$ | $R^8$ | X | M.p. [°C.] |
|---|---|---|---|---|---|---|---|---|---|
| 3 | H | H | 1 | H | H | H | 4-Cl—$C_6H_4$—$CH_2$— | Br | 177–179 |
| 4 | H | H | 1 | H | H | H | $CH_3$— | $NO_3$ | |
| 5 | 7-Cl | H | 1 | H | H | H | 1-$C_{10}H_7$—$CH_2$— | Cl | 225–227 |
| 6 | 7-Cl | H | 1 | H | H | H | 4-F—$C_6H_4$—$CH_2$— | Br | 218–220 |
| 7 | 7-Cl | H | 1 | H | H | $CH_3$ | 4-Cl$C_6H_4$—$CH_2$— | Br | |
| 8 | 7-Cl | H | 1 | H | H | H | 4-Cl$C_6H_4$—$CH_2$— | Br | 232–234 |
| 9 | 7-Cl | H | 1 | H | H | H | 4-Br$C_6H_4$—$CH_2$— | Br | 225–227 |
| 10 | 7-Cl | H | 1 | H | H | H | 2,4-$Cl_2C_6H_3$—$CH_2$— | Cl | 212–215 |
| 11 | 7-Cl | H | 1 | H | H | H | 4-($CH_3$)$C_6H_4$—$CH_2$— | Br | 210–212 |
| 12 | 7-Cl | H | 1 | H | H | H | 4-(tert-$C_4H_9$)$C_6H_4$—$CH_2$— | Br | 180–182 |
| 13 | 7-Cl | H | 1 | H | H | H | 4-($CF_3$)$C_6H_4$—$CH_2$— | Br | 224–226 |
| 14 | 7-Cl | H | 1 | H | H | H | 4-($NO_2$)$C_6H_4$—$CH_2$— | Br | 243–245 |
| 15 | 7-Cl | H | 1 | H | H | H | 4-(CN)$C_6H_4$—$CH_2$— | Br | |
| 16 | 7-Cl | H | 1 | H | H | H | $CH_2$=CH—$CH_2$— | Br | 145–147 |
| 17 | 7-Cl | H | 1 | H | H | H | $CH_3$—CH=CH—$CH_2$— | Br | 156–159 |
| 18 | 7-Cl | H | 1 | H | H | H | n-$C_4H_9$ | Br | 155–158 |
| 19 | 7-Cl | H | 1 | H | H | H | HC≡C—$CH_2$— | Br | |
| 20 | 7-Cl | $CH_3$ | 1 | H | H | H | $C_2H_5$— | I | |
| 21 | 7-Cl | $CH_3$ | 1 | H | H | H | $C_6H_5$—$CH_2$— | Br | 146–149 |
| 22 | 7-Cl | $CH_3$ | 1 | H | H | H | 4-($CH_3$)$C_6H_4$—$CH_2$— | Br | 175–178 |
| 23 | 7-Cl | $CH_3$ | 1 | H | H | H | 4-(tert-$C_4H_9$)$C_6H_4$—$CH_2$— | Br | 195–197 |
| 24 | 7-Cl | $CH_3$ | 1 | H | H | H | 2,4-$Cl_2C_6H_3$—$CH_2$— | Cl | 179–181 |
| 25 | 7-Cl | $CH_3$ | 1 | H | H | H | 2,4-$Cl_2C_6H_3$—O—$CH_2CH_2$— | Br | 145–146 |
| 26 | 7-Cl | $CH_3$ | 1 | H | H | H | 3-($NO_2$)$C_6H_4$—O—$CH_2$—$CH_2$— | Br | resin |
| 27 | 7-Cl | H | 1 | H | H | H | $C_6H_5$—O—$CH_2$—$CH_2$— | Br | 169–171 |
| 28 | 7-Cl | H | 1 | H | H | H | 3-($CH_3$)$C_6H_4$—O—$CH_2$—$CH_2$— | Br | 166–168 |
| 29 | 7-Cl | H | 1 | H | H | H | 3-($CF_3$)$C_6H_4$—O—$(CH_2)_4$— | Br | 116–121 |
| 30 | 7-Cl | H | 1 | H | H | H | 4-($NO_2$)$C_6H_4$—O—$CH_2$—$CH_2$— | Br | |
| 31 | 7-Cl | H | 2 | H | H | H | 4-Cl$C_6H_4$—$CH_2$— | Br | 164–166 |
| 32 | 7-Cl | H | 2 | H | H | H | 4-Br$C_6H_4$—O—$CH_2$—$CH_2$— | Br | 127–131 |
| 33 | 7-Cl | H | 2 | H | H | H | 4-F$C_6H_4$—O—$CH_2$—$CH_2$— | Br | resin |
| 34 | 7-Cl | H | 2 | H | H | H | 1-$C_{10}H_7$—$CH_2$—$CH_2$— | Br | resin |
| 35 | 7-Cl | H | 2 | H | H | H | 2-$C_{10}H_7$—O—$CH_2$—$CH_2$— | Br | resin |
| 36 | 7-Cl | H | 3 | H | H | H | HC≡C—$CH_2$— | Br | 136–138 |
| 37 | 7-Cl | $CH_3$ | 3 | H | H | H | $C_6H_5$—$CH_2$— | Br | resin |
| 38 | 7-Cl | H | 3 | H | H | H | $C_6H_5$—$CH_2$— | Br | 138–142 |
| 39 | 7-Cl | H | 3 | H | H | H | 4-Cl$C_6H_4$—$CH_2$— | Br | 196–199 |
| 40 | 7-Cl | H | 3 | H | H | H | 4-($CH_3$)$C_6H_4$—$CH_2$— | Br | 168–172 |
| 41 | 7-Cl | H | 3 | H | H | H | 4-(tert-$C_4H_9$)$C_6H_4$—$CH_2$— | Br | resin |
| 42 | 7-Cl | H | 1 | H | H | H | $C_6H_5$—CH=CH—$CH_2$— | Br | 176–178 |
| 43 | 7-Cl | H | 1 | H | H | H | $C_6H_5$—CH=$\overset{CH_3}{C}$—$CH_2$— | Br | |
| 44 | 7-Cl | H | 1 | H | H | H | 4-(tert-$C_4H_9$)$C_6H_4$—CH=$\overset{CH_3}{C}$—$CH_2$— | Br | 168–170 |
| 45 | 7-Cl | H | 1 | H | H | H | 4-($CH_3$O)$C_6H_4$—CH=CH—$CH_2$— | Br | |

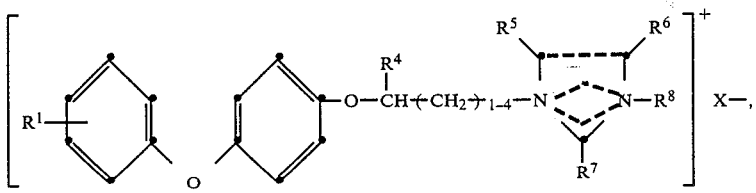

| No. | R¹ | R⁴ | m | R⁵ | R⁶ | R⁷ | R⁸ | X | M.p. [°C.] |
|---|---|---|---|---|---|---|---|---|---|
| 46 | 7-CH₃ | H | 1 | H | H | H | C₆H₅—O—(CH₂)₄— | Br | |
| 47 | 7-CH₃ | H | 1 | H | H | H | 4-ClC₆H₄—CH₂— | Br | |
| 48 | 7-F | H | 1 | H | H | CH₃ | C₆H₅—CH₂— | Cl | |
| 49 | 7-F | H | 3 | H | H | H | 4-ClC₆H₄—CH₂— | Br | 158–160 |
| 50 | 6-CF₃ | H | 1 | H | H | H | 4-ClC₆H₄—CH₂— | Br | 213–215 |
| 51 | 6,8-Cl₂, 7-CH₃ | H | 3 | H | H | H | 4-ClC₆H₄—CH₂— | Br | 210–212 |
| 52 | 6,7-Cl₂ | H | 1 | H | H | H | 4-ClC₆H₄—CH=CH—CH₂— | Br | |

The novel active ingredients have a strong fungitoxic action on phytopathogenic fungi. They are especially suitable for preventing and curing plant diseases caused by microorganisms, e.g., *Botrytis begonie, Botrytis cinerea, Plasmopara viticola, Monilia fructigena, Alternaria solani, Solerotinia solerotiorum, Piricularia oryzae, Pellicularia filamentosa, Erysiphe graminis, Erysiphe cichoriacearum, Chaetomium globosum, Sclerotinia cinerea, Aspergillus niger, Xanthomonas oryzae, Xanthomonas citri,* and *Phytophthora infestans* (in potatoes and tomatoes).

The active ingredients according to the invention may simultaneously suppress the growth of two or more of the above fungi, and are well tolerated by plants. Some of the active ingredients have curative properties, i.e., the agents may even be applied after the plants have been infected by the pathogen, and success is still achieved.

The fungicidal agents contain from 0.1 to 95, and preferably from 0.5 to 90, wt% of active ingredient. The application rates depend on the type of effect desired, and range from 0.1 to 5 kg of active ingredient per hectare.

The agents according to the invention may also be mixed and applied with other active ingredients, e.g., herbicides, insecticides, growth regulators, fungicides and fertilizers. When mixed with other fungicides, the spectrum of fungicidal action is in many cases increased; with a number of these fungicidal compositions, synergistic effects also occur, i.e., the fungicidal action of the combination product is greater than the effect of the individual components added together. The spectrum of action is particularly favorably influenced when the compounds according to the invention are mixed with the following fungicides: manganese N,N-ethylene-bis-dithiocarbamate, manganese zinc N,N-ethylenediamine-bis-dithiocarbamate, the ammonia complex of zinc N,N-ethylene-bis-dithiocarbamate and N,N'-polyethylene-bis-(thiocarbamoyl)-disulfide, N-trichloromethylthiotetrahydrophthalimide, N-trichloromethylthiophthalimide, 5-ethoxy-3-trichloromethyl-1,2,3-thiadiazole, 2-methoxycarbonylaminobenzimidazole, 2-thiocyanomethylthiobenzothiazole, 1,4-dichloro-2,5-dimethoxybenzene, 2,3-dichloro-6-methyl-1,4-oxathiin-5-carboxylic acid anilide, 2-methyl-5,6-dihydro-4H-pyran-3-carboxylic acid anilide, 2,4,5-trimethylfuran-3-carboxylic acid anilide, 2-methylfuran-3-carboxylic acid anilide, 2,5-dimethylfuran-3-carboxylic acid cyclohexylamide, N-cyclohexyl-N-methoxy-2,5-dimethylfuran-3-carboxylic acid amide, 5-methyl-5-vinyl-3-(3,5-dichlorophenyl)-2,4-dioxo-1,3-oxazolidine, and 3-(3,5-dichlorophenyl)-5-methyl-5-methoxymethyl)-1,3-oxazolidine-2,4-dione.

However, the compounds according to the invention may also be combined with the following fungicides: dithiocarbamates and their derivatives, e.g. iron(III)-dimethyldithiocarbamate, zinc dimethyldithiocarbamate, zinc N,N-ethylene-bis-dithiocarbamate, tetramethylthiuram disulfide, zinc N,N-propylene-bis-dithiocarbamate, and the ammonia complex of zinc N,N-propylene-bis-dithiocarbamate and N,N'-polypropylene-bis-(thiocarbamoyl)-disulfide, nitro derivatives, e.g. dinitro-(1-methylheptyl)-phenyl crotonate, 2-sec.-butyl-4,6-dinitrophenyl-3,3-dimethylacrylate and 2-sec.-butyl-4,6-dinitrophenyl isopropyl carbonate; heterocyclic compounds, e.g. 2-heptadecyl-2-imidazoline acetate, 2,4-dichloro-6-(o-chloroanilino)-s-triazine, O,O-diethylphthalimidophosphonothioate, 5-amino-1-[bis-(dimethylamino)-phosphinyl]-3-phenyl-1,2,4-triazole, 2,3-dicyano-1,4-dithioanthraquinone, 2-thio-1,3-dithio(4,5-b)-quinoxaline, methyl 1-(butylcarbamoyl)-2-benzimidazole-carbamate, 4-(2-chlorophenylhydrazono)-3-methyl-5-isoxazolone, pyridine-2-thio-1-oxide, 8-hydroxyquinoline and its copper salt, 2,3-dihydro-5-carboxanilido-6-methyl-1,4-oxathiine-4,4-dioxide, 2,3-dihyro-5-carboxanilido-6-methyl-1,4-oxathiine, 2-fur-2-yl-benzimidazole, piperazine-1,4-diyl-bis-[1-(2,2,2-trichloroethyl)-formamide], 2-thiazol-4-yl-benzimidazole, 5-butyl-2-dimethylamino-4-hydroxy-6-methylpyridine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-[2-(3,5-dimethyl-2-hydroxy-cyclohexyl)-2-hydroxyethyl]-glutarimide, hexachlorobenzene, N-dichlorofluoromethylthio-N',N'-dimethyl-N-phenylsulfuric acid diamide, 2,5-dimethyl-furan-3-carboxylic acid anilide, 2-methyl-benzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, alpha-(2-chloro-phenyl)-alpha-(4-chlorophenyl)-5-pyrimidine-methanol, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, DL-methyl-N-(2,6-dimethyl-phenyl)-N-furoyl(2)-alanate, methyl DL-N-(2,6-dimethyl-phenyl)-N-(2'-methoxyacetyl)-alanate, diisopropyl 5-nitroisophthalate, N-(2,6-dimethylphenyl)-N- chloroacetyl-D,L-2-aminobutyrolactone, N-(n-propyl)-N-(2,4,6-trichlorophenoxyethyl)-N'-imidazolylurea, N-cyclohexyl-N-methoxy-2,5-dimethyl-furan-3-carboxylic acid amide, 2,4,5-trimethyl-furan-3-carboxanilide, 5-methyl-5-vinyl-3-(3,5-dichlorophenyl)-2,4-dioxo-1,3-oxazolidine, 5-methoxymethyl-5-methyl-3-(3,5-dichlorophenyl)-2,4-dioxo-1,3-oxazolidine, N-[3-(p-tert.-butylphenyl)-2-methyl-propyl]-cis-2,6-dime/thyl-morpholine, N-formyl-N-morpholine-2,2,2-trichloroethylacetal, 1-[2-(2,4-dichlorophenyl)-4-ethyl-1,3-dioxolan-2-yl-methyl]-1H-1,2,4-triazole, 1-[2-(2,4-dichlorophenyl)-4-n-propyl-1,3-dioxolan-2-yl-methyl]-1H-1,2,4-triazole, 2-(thiocyanomethylthio)-benzthiazole, 1-[2-(2,4-dichlorophenyl)-2-(2-propenyl-oxy)-ethyl]-1H-imidazole, 2,4,5,6-tetrachloroisophthalodinitrile, methylene-bis-thiocyanate, tributyl tin oxide, mercaptobenzthiazole, benzisothiazolone and its alkali metal salts, alkali compounds of N'-hydroxy-N-cyclohexyl-diazenium oxide, 2-(methoxy-carbonylamino)-benzimidazole, 2-methyl-3-oxo-5-chlorothiazolin-3-one, trihydroxymethyl-nitromethane, glutardialdehyde, and chloroacetamide.

The novel active ingredients are applied for instance in the form of directly sprayable solutions, suspensions, emulsions (including high-percentage aqueous, oily or other dispersions), pastes, dusts, broadcasting agents, or granules by spraying, atomizing, dusting, broadcasting or watering. The forms of application depend entirely on the purpose for which the agents are being used, but generally they should ensure a fine distribution of the active ingredient.

For the preparation of solutions, emulsions, pastes and oil dispersions to be sprayed direct or after emulsification in water, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

Examples of such crop protection agent formulations are given below.

I. 90 parts by weight of the compound of Example 1 is mixed with 10 parts by weight of N-methyl-alpha-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of the compound obtainable in accordance with Example 13 is dissolved in a mixture consisting of 30 parts by weight of cyclohexanone, 30 parts by weight of isobutanol, and 20 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of the compound obtainable in accordance with Example 14 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of the compound obtainable in accordance with Example 21 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 5 parts by weight of the compound obtainable in accordance with Example 25 is intimately mixed with 95 parts by weight of particulate kaolin. A dust is obtained containing 5% by weight of the active ingredient.

VII. 30 parts by weight of the compound obtainable in accordance with Example 37 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of the compound obtainable in accordance with Example 42 is intimately mixed with 30 parts of the sodium salt of a phenolsulfonic acid-urea-formaldehyde condensate, 2 parts of silica gel and 48 parts of water to give a stable aqueous dispersion.

IX. 20 parts of the compound obtainable in accordance with Example 51 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The imidazolium salts according to the invention are also suitable for industrial purposes, e.g., as wood preservatives. The compounds have also been found to have not only a fungicidal action, but also a bactericidal action—they are also suitable as such for use in crop protection and as industrial microbicides; they are also suitable for external use in human and veterinary medicine. For instance the following microorganisms may be combated:

Staphylococcus aureus, Escherichia coli, Klebsiella pneumoniae, Citrobacter freundii, Proteus vulgaris, Pseudomonas aeruginosa, Pseudomonas fluorescens, Xanthomonas vesicatoria, Xanthomonas malvaccarum, Erwinia carotovora, Erwinia amylovora, Desulfovibrio desulfuricans, Streptoverticillium rubrireticuli, Aspergillus niger, Aspergillus versicolor, Penicillium funiculosum, Paecilomyces variotii, Trichoderma viride, Chaetomium globosum, Candida albicans, Geotrichum candidans, Monilia sitophila, Scenedesmus quadricauda, Chlorella vulgaris, and Nostoc muscorum.

The usual use concentrations are from 0.01 to 1% of active ingredient, based on the weight of the material to be protected; when the active ingredients are used for water treatment in oil production, in swimming baths, cooling towers, air humidifying units, flower preservatives or in the paper industry, amounts of from 5 to 100 ppm are sufficient to suppress microorganism development. Ready-to-use disinfectant solutions contain from 0.2 to 5% of active ingredient.

Examples 53 to 56 demonstrate the biological action of the novel compounds. The comparative agent employed in all cases is the prior art active ingredient N-trichloromethylthiotetrahydrophthalimide (Chem. Week, June 21, 1972, p. 46), which is especially suitable for combating Botrytis.

EXAMPLE 53

Action on *Botrytis cinerea* in pimientos

Pimiento seedlings of the "Neusiedler Ideal Elite" variety were sprayed, after 4 to 5 leaves were well developed, to runoff with 0.05% aqueous suspensions containing (dry basis) 80% of active ingredient and 20% of emulsifier. After the sprayed-on layer had dried, the plants were sprinkled with a conidial suspension of the fungus Botrytis cinerea, and placed at 22° to 24° C. in a chamber of high humidity. After 5 days, the disease had spread to such a great extent on the untreated plants that the necroses covered the major portion of the leaves.

| Active ingredient | Attack |
|---|---|
| 5 | 0 |
| 6 | 1 |
| 8 | 1 |
| 9 | 0 |
| 10 | 0 |
| 11 | 0 |
| 12 | 0 |
| 13 | 1 |
| 14 | 0 |
| 22 | 2 |
| 23 | 0 |
| 24 | 1 |
| 25 | 1 |
| 26 | 0 |
| 32 | 1 |
| 33 | 1 |
| 35 | 0 |
| 41 | 1 |
| 44 | 1 |
| Comparative agent | 3 |
| Untreated | 5 |

Assesement:
0 = no fungus attack graduated down to
5 = total attack

EXAMPLE 54

Action of *Phytophthora infestans* in tomatoes

Leaves of potted tomatoes of the "Große Fleischtomate" variety were sprayed with a 0.025% aqueous liquor containing (dry basis) 80% of active ingredient and 20% of emulsifier. After the sprayed-on layer had dried, the leaves were infected with a zoospore susplension of *Phytophthora infestans*. The plants were then placed for 5 days in a steam-saturated chamber kept at 16° to 18° C. After this period, the disease had spread on the untreated control plants to such an extent that the fungicidal action of the compounds were able to be assessed.

| Active ingredient | Attack |
|---|---|
| 5 | 2 |
| 6 | 1 |
| 9 | 0 |
| 10 | 0 |
| 14 | 1 |
| 21 | 0 |
| 22 | 1 |
| 24 | 2 |
| 25 | 1 |
| 26 | 2 |
| 32 | 1 |
| 36 | 2 |
| 38 | 2 |
| 39 | 1 |
| 40 | 1 |
| 41 | 1 |
| 44 | 1 |
| Comparative agent | 3 to 4 |
| Untreated | 5 |

Assessment:
0 = no fungus attack, graduated down to
5 = total attack

EXAMPLE 55

To determine the action on fungi, the active ingredients were added, in amounts of 200, 100, 50, 25, 12, 6 and 3 parts per million parts of solution, to a nutrient solution ideally suited for promoting the growth of the fungi *Candida albicans, Aspergillus niger* and *Oidium lactis*. 10 ml of the mixture of nutrient solution and active ingredient was introduced into sterile test tubes and inoculated with one drop of a spore suspension containing $10^6$ conidia or cells. After 120 hours' incubation, samples were taken from those tubes exhibiting no visible fungus growth and transferred to fungus nutrient media.

The table below contains the highest dilution stage at which there is no more fungus growth, i.e., the minimum inhibition concentration.

| Active ingredient | Minimum inhibition concentration (parts of active ingredient per million parts of nutrient solution) | | |
|---|---|---|---|
| | *Aspergillus niger* | *Oidium lactis* | *Candida albicans* |
| 6 | 50 | 6 | 12 |
| 10 | 200 | 6 | 6 |
| 18 | 200 | 12 | 25 |
| 25 | 100 | 12 | 12 |
| 26 | 25 | 6 | 6 |
| 32 | 50 | 6 | 6 |
| 39 | 50 | 6 | 6 |

EXAMPLE 26

To determine the action on bacteria, 5 ml of increasing dilutions of the active ingredients was added to 5 ml of nutrient broth in sterile test tubes, and mixed. The tubes were then inoculated by adding one drop of a 16-hour old broth culture (diluted 1:10) of the bacteria species *Staphylococcus aureus, Escherichia coli,* or *Proteus vulgaris,* and incubated for 24 hours at 37° C. After this time, samples were transferred from the tubes to bacteria nutrient media which were then also incubated for 24 hours at 37° C.

The table below contains the highest dilution stage at which there is no more bacterial growth, i.e., the minimum inhibition concentration.

| Active ingredient | Minimum inhibition concentration (parts of active ingredient per million parts of nutrient broth) | | |
|---|---|---|---|
| | *Staphylococcus aureus* | *Escherichia coli* | *Proteus vulgaris* |
| 6 | 6 | 6 | 12 |
| 10 | 6 | 6 | 6 |
| 18 | 6 | 50 | 25 |
| 25 | 6 | 12 | 12 |
| 26 | 6 | 25 | 25 |
| 32 | 6 | 12 | 12 |
| 39 | 12 | 12 | 12 |

We claim:

1. A dibenzofuranyloxyalkylimidazolium salt of the formula

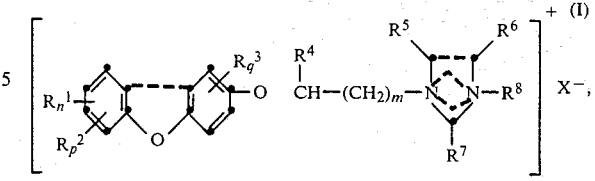

where $R^1$, $R^2$ and $R^3$ are identical or different and are each halogen, unsubstituted or halogen-substituted alkyl or alkoxy, each of 1 to 4 carbon atoms, cyano or nitro, $R^4$, $R^5$, $R^6$ and $R^7$ independently of one another are each hydrogen or alkyl of 1 to 4 carbon atoms, $R^8$ is alkyl, alkenyl or alkynyl, each of not more than 6 carbon atoms, $$-CH_2-Ar, -CH_2-\overset{R^4}{\underset{|}{C}}=CH-Ar \text{ or } -(CH_2)_{2-5}-O-Ar,$$

Ar is naphth-1-yl, naphth-2-yl, biphenylyl or phenyl, and the phenyl radical can be substituted by fluorine, chlorine, bromine, nitro, trifluoromethyl, cyano or alkyl, alkenyl or alkoxy of not more than 5 carbon atoms, m is 1, 2, 3 or 4, n, p and q are each 0, 1, 2 or 3, and X is an anion of a monobasic, non-phytotoxic acid or one equivalent of an anion of a polybasic, non-phytotoxic acid.

2. A dibenzofuranyloxyalkylimidazolium salt as claimed in claim 1, wherein $R^1$, $R^2$, $R^3$ are halogen, alkyl or alkoxy of 1 to 4 carbon atoms, trifluoromethyl or nitro, m is 1, 2, 3 or 4, n is 0, 1, 2 or 3, p and q are each 0, $R^4$, $R^5$, $R^6$ and $R^7$ are each hydrogen, methyl or ethyl, $R^8$ is methyl, ethyl, n-propyl, n-butyl, isobutyl, n-pentyl, isopentyl, n-hexyl, vinyl, allyl, but-2-en-1-yl, 3-methyl-but-2-en-1-yl or propargyl, or is $$-CH_2-Ar, -CH_2-\underset{\underset{R^4}{|}}{C}=CH-Ar \text{ or } -(CH_2)_{2-5}-O-Ar,$$

Ar being naphth-1-yl, naphth-2-yl, biphenylyl, phenyl, 4-fluorophenyl, 3-chlorophenyl, 4-chlorophenyl, 4-bromophenyl, 3,4-dichlorophenyl, 2,4-dichlorophenyl, 2,6-dichlorophenyl, 2-methyl-4-chlorophenyl, 4-methoxyphenyl, 4-ethoxyphenyl, 4-methylphenyl, 4-isopropylphenyl, 4-tert.-butylphenyl, 4-nitrophenyl, 4-trifluoromethylphenyl, 2,4-dimethylphenyl or 4-cyanophenyl and X is an anion, or one equivalent of an anion, of a non-phytotoxic acid.

3. A composition for crop protection having fungicidal and bactericidal properties comprising inert additives and, as active ingredient, a dibenzofuranyloxyalkylimidazolium salt as claimed in claim 1.

4. A method for combating fungi and bacteria, wherein a dibenzofuranyloxyalkylimidazolium salt as claimed in claim 1 is allowed to act thereon, or on areas, plants, seed, wood, or human or animal skin threatened by bacterial or fungal attack.

* * * * *